(12) United States Patent
Erhardt et al.

(10) Patent No.: US 8,409,854 B2
(45) Date of Patent: Apr. 2, 2013

(54) BIOREACTOR PROVIDED WITH EQUIPMENT WITH FLEXIBLE WALLS

(75) Inventors: Ursula Erhardt, Berlin (DE); Christoph Erhardt, Berlin (DE)

(73) Assignee: Sartorius Stedim Biotech GmbH (DE)

( * ) Notice: Subject to any disclaimer, the term of this patent is extended or adjusted under 35 U.S.C. 154(b) by 572 days.

(21) Appl. No.: 10/485,602

(22) PCT Filed: Jul. 31, 2001

(86) PCT No.: PCT/DE01/02901
§ 371 (c)(1), (2), (4) Date: Jan. 24, 2005

(87) PCT Pub. No.: WO03/012027
PCT Pub. Date: Feb. 13, 2003

(65) Prior Publication Data
US 2005/0130291 A1    Jun. 16, 2005

(51) Int. Cl.
*C12M 1/14* (2006.01)
*C12M 3/04* (2006.01)

(52) U.S. Cl. ............... 435/299.2; 435/289.1; 435/299.1; 435/304.2; 435/809; 435/303.1

(58) Field of Classification Search ............... 435/289.1, 435/299.2, 299.1, 304.2, 304.1, 809, 303.1
See application file for complete search history.

(56) References Cited

U.S. PATENT DOCUMENTS

| 4,207,007 | A | * | 6/1980 | Yamschikov et al. | 366/275 |
| 4,550,653 | A | * | 11/1985 | Hedenberg | 99/348 |
| 4,665,035 | A | | 5/1987 | Tunac | |
| 6,844,186 | B2 | * | 1/2005 | Carll | 435/289.1 |
| 2004/0062140 | A1 | * | 4/2004 | Cadogan et al. | 366/144 |
| 2010/0015696 | A1 | * | 1/2010 | Claes et al. | 435/303.3 |

FOREIGN PATENT DOCUMENTS

| GB | 2 182 647 A | 5/1987 |
| JP | 06-253815 | 9/1994 |

OTHER PUBLICATIONS

Fisher Labware Katalog, 2001, pp. 248-251.

* cited by examiner

*Primary Examiner* — Nathan Bowers
(74) *Attorney, Agent, or Firm* — Gerald E. Hespos; Michael J. Porco; Matthew T. Hespos

(57) ABSTRACT

A bioreactor comprising a reactor chamber defined by reactor walls and a reactor opening, optionally with means penetrating the reactor opening in order to supply gases and/or liquids, for taking samples, for supplying microorganisms or cells, for the introduction of measuring probes, for the addition of additives or sterilizing agents and/or for emptying the bioreactor, with means for sealing the reactor opening, wherein at least one inflatable eddy current breaker is installed in the reactor chamber.

12 Claims, 8 Drawing Sheets

BIOREACTOR PROVIDED WITH EQUIPMENT WITH FLEXIBLE WALLS

FIELD OF THE INVENTION

The invention relates to a bioreactor or a culture vessel for use in the cultivation of microorganisms, cells or cell-free expression systems. Bioreactors are used in sectors, where biological or biochemical reactions are performed, in particular in the sectors biotechnology, food technology and environmental protection.

PRIOR ART

The fermentation technology has made substantial progress in the last twenty years particularly in the sector of cultivation of (newly gene-combined) microorganisms and cells. It is the aim to provide as economically as possible production methods and method developments for the cultivation of cells and microorganisms by maximum yields. The limiting factor is not the content of the nutrient, but the technical equipment of the culture vessels securing the supply and the mixing of gases and liquids. The cultivation starts in most cases with an inoculation of small culture bottles with 10 ml size, and is continued in systems of up to 1,000 $m^3$ with high technological equipment. The method development, even for larger systems, is performed, for cost reasons, as far as possible in small culture bottles. The method development in small culture vessels relates, however, in most cases only to the optimization of the medium components, not however to amount and re-feeding intervals, since the culture vessels and their technical equipment are very different. The culture conditions are so different and not at all comparable that during scale-up, a re-optimization is in every case necessary.

State-of-the-art devices (reactors) in the size of 0.001 $m^3$ to 1,000 $m^3$ fermenters are reaction containers of glass or in most cases stainless steel in the size of 1 liter to several 100 cubic meters working volume. In the production scale, they serve for a controlled execution of biological or biochemical reactions in the biotechnology, the food industry and wastewater cleaning. Three major components can be identified:

a) The Reaction Container

In most cases, the container is an agitated container with built-in agitator shaft and stirring wings, with or without eddy current breakers (chicanes). Further, the mixing of the medium may take place by external or internal liquid loops being operated by air or pumps. Gassing takes place through air ejector tubes or air ejector rings. Measuring probes are introduced through threaded ports at the side or in the cover.

b) Supply Equipment

Reaction conditions are maintained by the use of supply equipment provided beside the reaction container. To this belongs, among other equipment, the agitator drive, the tempering and the dosing sections for pH control or substrate dosage and for the control of aeration.

c) Measurement and Control Equipment

In a switch cabinet arranged beside the reaction container and the supply equipment are accommodated the measurement and control equipment or an EDP-supported process control system securing and recording that the reaction conditions in the reactor are maintained.

In order to operate a fermenter economically in production, the optimum reaction conditions have to be determined in quite a number of pre-tests. The high technical and economical efforts exclude the use of fermenters for these pre-tests (e.g. medium optimization), so that the culture vessels described below, mainly shaken Erlenmeyer flasks, are employed.

The state of the art of culture vessels as known from practical applications is the following. The culture vessels used for microorganisms are shaken in the size 10 ml to 5,000 ml volume under tempered conditions either on suitable shaking devices or on magnetic stirrers. The most used culture vessel, among a multitude of culture vessels, is the Erlenmeyer flask (see Fisher Scientific catalog, page 249 ff) in a size of 10 ml to 1,000 ml. They are pure 2-phase systems, since an aeration of the culture vessel does not take place. By the circular movement of the stirrer, a circle flow being in most cases laminar, is generated in the reaction liquid, said circle flow securing poor mixing only. Although Erlenmeyer flasks equipped with eddy current breakers (chicanes) pressed-in within the glass can be used, in order to generate a turbulent mixing of the reaction liquid, the gas exchange in the liquid is nevertheless limited, since the gas exchange can only take place at the phase border between liquid and headspace (air above) in a diffusion-controlled manner. An addition of the third phase (gas) is lacking. The effectivity compared to three-phase systems is below 1%. A re-supply of unused inlet air is achieved by diffusion through static filter systems or by diffusion under a steel cap and also is a limiting step. Nor are there possibilities for a controlled liquid dosage or the introduction of measuring probes. Due to the geometry of the Erlenmeyer flasks (narrow neck), the incorporation of stationary constructs in the reaction chamber is substantially limited. The capacities of large reactors cannot nearly be simulated, and defined and reproducible conditions, as they are required for recoding the reaction or for a scale-up in large reactors, cannot be achieved thereby.

Further are used so-called bubble columns in the form of culture bottles (see Fisher Scientific catalog, p. 248), wherein a porous plate replaces the glass bottom, and through which the air is blown into the culture bottle. This kind of gassing (three-phase system) is more efficient than the above 2-phase system, however the blow-in direction (bubbles pass the liquid on a shorter way) towards top limits the aeration rate because of the shorter contact time and the promotion of foam generation, the lacking circle movement by shaking or stirring, and the lacking eddy current breakers (chicanes) also reduce the effectivity of the mixing of the reaction liquid (Infors homepage www.Infors.ch/d/d5a.htm). With regard to flow properties, bubble columns are thus extremely unfavorable, since in many cases only a laminar upward movement of the liquid is generated. By a lateral glass port, if applicable, a pH probe for measuring the pH value can be introduced, and taking a sample of the reaction liquid can be performed.

In the sector of the cultivation of cells, stirred "spinners", i.e. glass vessels with a magnetic stirring bar suspended from the cover, are used (see Fisher Scientific catalog, p. 251). Drive takes place from below by a magnetic stirrer arranged underneath the vessel. Eddy current breakers (chicanes) or aeration systems in the form of constructs are not present, and are not possible because of the geometry, similar to an Erlenmeyer flask. Thus, the stirring bar only generates an extremely inefficient, frequently laminar cycle flow, with the disadvantage of poor mixing. By a lateral glass port, if applicable, a pH probe for measuring the pH value can be introduced, and taking a sample of the reaction liquid can be performed.

As a summary, using culture vessels has the following problems and disadvantages:

No comparability to large fermenters.

No optimum supply with gases or liquids.

No documentation of the process.
No reproducibility.

Several companies (e.g. Infors AG, www.Infors.ch/d/d5a.htm or Das GIP GmbH, www.dasgip.de) recently offered "cross solutions", wherein a supply equipment and an EDP-supported measurement and control unit parallely operates several small fermenters or up to 16 culture vessels. This permits to reduce the economical and technical expenses, and to reduce the time for the pre-tests by parallel processes. It is disadvantageous here, too, that the reaction conditions, in particular because of the culture vessels, cannot be compared to the reaction conditions of the fermenters, and thus the optimization is insufficient only. An oxygen supply rate, which may be 100 times larger in the fermenter than in the shaken Erlenmeyer flask, will lead to completely different metabolic conditions of the organism, and affects the previously optimized composition of the medium and production rate.

Technical Object

It is therefore the object of the invention to specify a bioreactor or a culture vessel for the laboratory scale, which provides optimum and reproducible cultivation results and is in particular easy to scale-up, i.e. provides conditions for the production scale without expensive re-optimizations.

Basics of the Invention

For achieving the above technical object, the invention teaches an inflatable or unfoldable equipment, which is installed in shaken or stirred culture vessels for biological and (bio)chemical reactions or represents the culture vessel itself, and is provided with suitable devices for generating a turbulent mixing and/or for gassing and/or for dosing into this culture vessel and/or for fixing measuring transducers (probe armature) in the culture vessel. By an unfoldable or inflatable insert, which, specially adjusted to the application, is installed in conventional culture vessels or represents a complete culture vessel, for the first time a method development and simulation under optimum gassing and dosing conditions is made possible, same as a bubble-free aeration of cell cultures, special complicated methods such as fed batch or dialysis fermentations. The yield of pre-cultures is substantially increased; the processes performed with the equipment according to the invention are comparable with regard to measurement and control as well as process control to production processes.

None of the lab scale vessels of the prior art use the constructs according to the present invention, which secures an efficient, turbulent mixing of the reaction liquid with eddy current breakers (chicanes) under utilization of the circular movement of the shaker and simultaneously allows the possibility for an effective aeration (flow-out direction of the gas toward bottom, thus: the bubbles move from below direction circular movement and are turbulently mixed at the eddy current breakers, the tendency to foam generation minimized) and the possibility for dosage sections, sample taking and introduction of measuring probes. A novel feature is further the technology of inflating or unfolding permitting to introduce the equipment through narrow openings in any type of vessel, and to adjust to any type of vessel. Thus the invention permits to use with smallest efforts extremely efficient and arbitrarily optimized reaction vessels exceeding the prior art by several orders of magnitude.

The present invention solves the scale-up problems described for the prior art, since the equipment according to the invention for culture vessels permits to set-up reaction, measurement and control conditions analogous to fermenters, and thus an immediate comparability of the results of the pre-tests for the later production is given. This results in drastic time and cost benefits when developing new production methods and permits high yield increases of the pre-cultures.

DETAILED DESCRIPTION OF THE INVENTION

Figure 1:
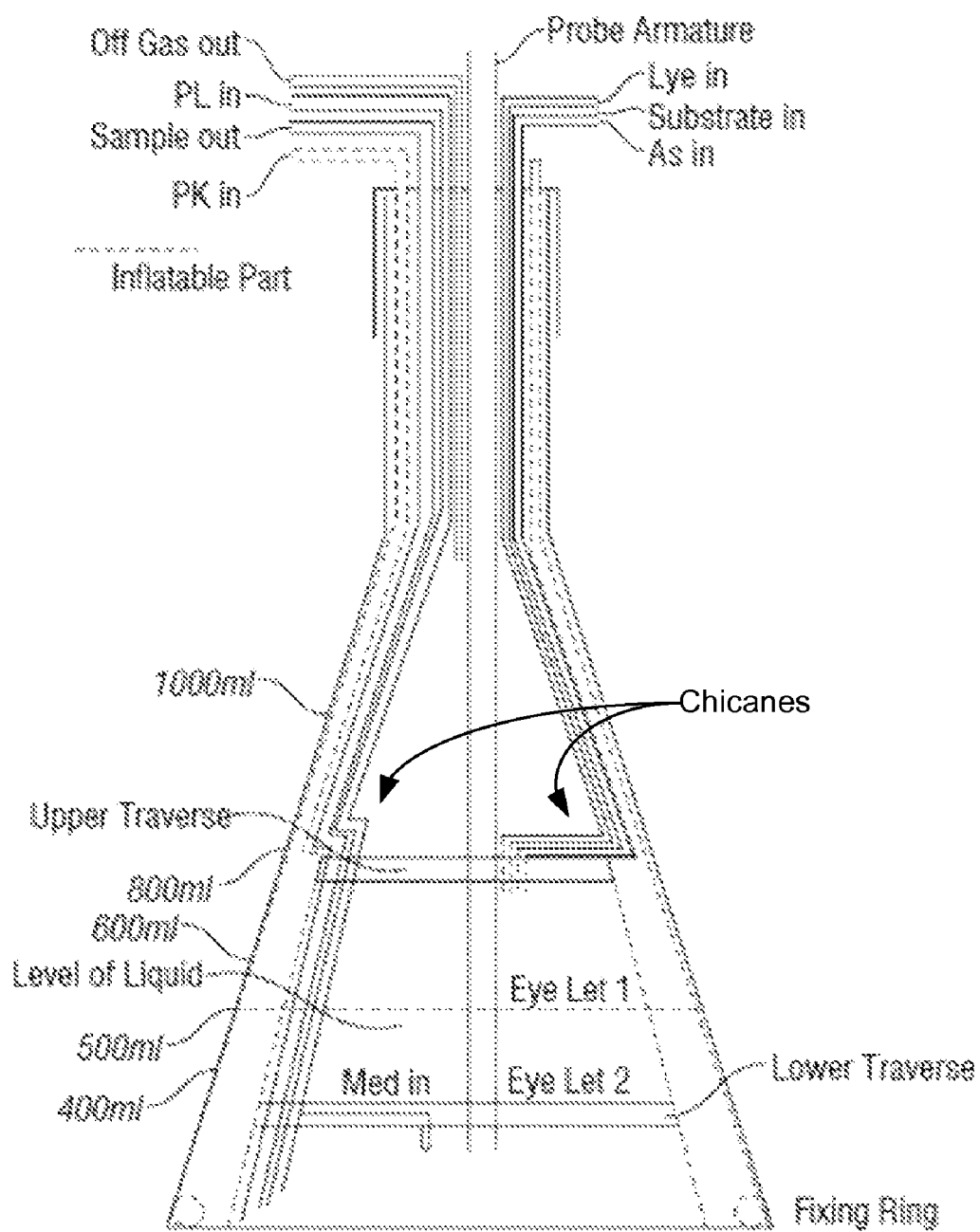
FIG. 1 shows the diagrammatical structure of a 1,000 ml Erlenmeyer flask with a reaction volume of 500 ml.
Figure 2:
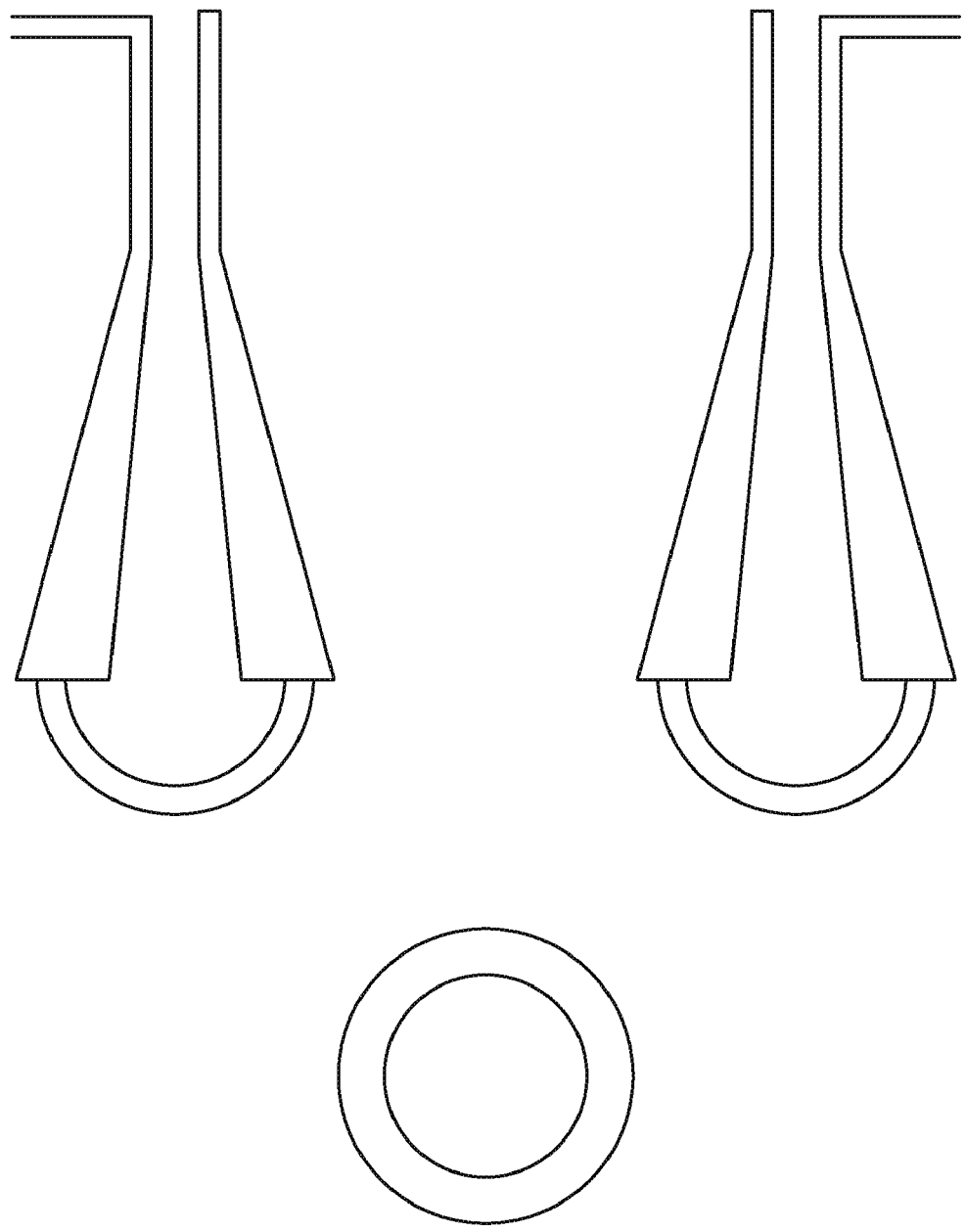
FIG. 2 illustrates the shape of exemplary cut pieces which may be employed as described to yield an inflatable or unfoldable insert for a culture vessel.

The present invention comprises an equipment used as an inflatable or unfoldable insert in arbitrary culture vessels (e.g. narrow-neck flasks) and adjusted to arbitrary culture vessels by its construction resulting after inflating or unfolding and by cutting the films, and designing the reaction conditions in the culture vessel at the first time in an optimum manner and making them comparable in a simple way with the reaction conditions of large reactors. The increase of volume from the not inflated or unfolded equipment to the final structure may be up to 100 times the volume. Thus, handling and storing of the equipment is appreciably simplified.

The present invention may accept (is however not necessarily so) several functions in the culture vessel. A survey of the construction is shown in the enclosed diagrammatical drawing 1.

Eddy Current Breakers (Chicanes)

The equipment is composed of extensible or not extensible synthetic or natural polymers and at least one, preferably two, at most 16 chicanes installed at a defined angle, 0 to 180 degrees, preferably 70 to 10 degrees, in particular 90 degrees, to the circular flow generated by the shaking device or stirrer. It generates a turbulent mixing of the reaction liquid in the section of the chicane(s). For increasing the turbulences, the chicane(s) may be perforated (nozzle effect) (hole size 1 to 20% of the chicane diameter, preferably 2 to 10%, in particular 5%) and/or have an undercut, i.e. a certain distance to the vessel wall (distance 1 to 20% of the chicane diameter, preferably 2 to 10%, in particular 5%). The chicane(s) is/are built up of a film cut according to the desired vessel geometry, said film then changing at the top into the inflation hose (PK in). The optimum diameter of the chicane is 10 to 30%, preferably 10 to 20%, in particular 15% of the diameter of the culture vessel. For a better fixation of the equipment, at the bottom of the vessel, an equally inflatable fixing ring having a diameter of 2 to 16 mm, preferably 4 mm, or a double-T fixing piece adjusted to the shape of the vessel is arranged. This will also provide for the pressure compensation in the individual chicanes. For improving the stability, several chicanes are connected by one or several traverses also being inflatable. These traverses prevent a "folding-over" of the chicanes in case of a too high flow-against force caused by the reaction liquid. For further stiffening of the chicanes, a rail may be welded at the rear in the film of the chicane, or a re-usable insert may be used for fixing the equipment. The eddy current breakers are sealed at one opening prior to the start of the reaction and inflated at the other opening with process gas, preferably air, having a pressure of 0.1 to 3 bars, preferably 0.5 bar, and then the other opening is sealed in order to maintain the shape generated by the pressure.

Furthermore, the eddy current breakers make possible the bubble-free aeration or de-aeration of the reaction liquid often desired for the cultivation of cells. Herein, the aeration/de-aeration does not take place with the air flowed into the reaction chamber (see below), but by diffusion of the gas from the cavity of the eddy current breaker through the plastic film or defined parts thereof, preferably silicone for this application, into the reaction liquid or out of the reaction liquid. In this application, the inflation and outlet openings are not sealed, but through the inflation opening gas is continuously supplied and constantly held by a pressure regulator at the outlet opening below a pressure of 0.2 to 3 bars, preferably 0.5 bar. Another special form of the bubble-free aeration is the replacement of the gas by liquids with otherwise identical construction. Some liquids have appreciably higher gas solubilities than water. If such a liquid is used as a carrier for gas, e.g. perfluorated hydrocarbons have very high oxygen solubilities, a diffusion gradient relative to the reaction liquid will be generated, which causes desired gas to diffuses in, e.g. $O_2$, or in the opposite case gases generated in the reaction liquid to diffuse out, e.g. $CO_2$. Further, it is possible to make the films of the eddy current breakers or parts thereof from polymers being permeable for substances having a defined molecule size. In this way, a supply or discharge of substances to the reaction liquid or out of the latter can take place from the liquid keeping the eddy current breakers in shape, as mentioned above. As an example, the refeeding of cell cultures with glucose with simultaneous removal of the disturbing lactate is mentioned here.

If several equipment units are used in a culture vessel, it is possible, for example, to perform a bubble-free aeration with one equipment unit and to supply substrate by another equipment unit through an integrated molecular sieve, both equipment units fulfilling the function of the eddy current breakers according to the invention.

For increasing the exchange surface accessible to the diffusion process, the otherwise smooth surface of the equipment may be increased by villi, fibers, folds, lamellae or other geometric shapes increasing the surface.

If the fluid flowing through the equipment is tempered, the equipment operates as a heat exchanger and thus makes a precise temperature regulation of the culture vessel possible in lieu of otherwise usual tempering devices.

Aeration System

In the film from which the eddy current breakers are formed, a duct of 1 to 5 mm, preferably 2 mm is welded in beside the eddy current breakers, and said duct can be provided at the top at the cover passage with a sterile filter for the sterile aeration of the system, and terminates at the bottom, directed toward the bottom of the culture vessel, in the reaction liquid. The bottom opening is fixed at the lower traverse. Through this duct, the third phase, the gas (PI in) is supplied to the reaction chamber. In lieu of producing the duct by welding, a suitable hose can be welded in or on.

Sampling System

In an analogous way to the aeration system, a duct having suitable dimensions is welded in beside the eddy current breakers, and said duct terminates at the bottom of the culture vessel and is open behind the cover passage. Through this duct, an aliquot of the reaction liquid can be taken as often as desired with a disposable syringe (sample out).

In lieu of producing the duct by welding, a suitable hose can be welded in or on.

Off Air System

In an analogous way to the aeration system, a duct having suitable dimensions is welded in beside the eddy current breakers, and said duct terminates in the upper air chamber of the culture vessel and is open behind the cover passage. Through this duct, off air can be taken from the air chamber above the reaction liquid, e.g. in order to determine the gas exchange rate of the reaction. In lieu of producing the duct by welding, a suitable hose can be welded in or on.

Dosing Sections

In an analogous way to the aeration system, three ducts having suitable dimensions are welded in at the opposite eddy current breaker, through which arbitrary liquids, such as substrate, lye, foam abatement agents can be dosed into the reaction liquid. Outside the cover passage, an arbitrary dosing device can be connected; the ducts terminate at the upper traverse shortly above or underneath the level of liquid. In lieu of producing the duct by welding, a suitable hose can be welded in or on.

Probe Armature

The probe armature is a tube, which is fixed at the passage of the cover opening and by eyelets at the traverses. The diameter is 2 to 25 mm, preferably 8 mm. By the armature, suitable measuring probes, such as pH probes, $pO_2$ probes, turbidity measurement, level sensor for liquid volume or foam detection, can be installed immediately in the reaction liquid. Sealing toward the equipment takes place by O-rings or welding-in of the probes. If a direct contact of the probe with the reaction liquid is not desired, the probes can be separated by a membrane from the reaction liquid. The membrane has to make possible the diffusion of the substances to be measured, yet also provide a sterile separation toward the reaction liquid. For instance, hereby the measurement of dissolved oxygen in sterile reaction liquids with unsterile $pO_2$ probes is made possible.

The description of an embodiment of the invention is given for a 1,000 ml Erlenmeyer flask with a reaction volume of 500 ml. It is specifically noted here that this description can simply be transferred to other culture vessels having different geometries and volumes (10 to 5,000 ml). The diagrammatical structure is shown in FIG. 1.

From a plastic film having a thickness between 0.1 to 4 mm, preferably 0.5 to 2 mm, in particular 1 mm, two symmetric pieces according to cut drawing 2 and the respective fixing ring and the two traverses are cut. The selection of the plastic material, preferably polyurethane, and the kind of connection (hot sealing, cold sealing, gluing, welding, ultrasonic welding), preferably hot sealing, depends on the pretreatment (e.g. sterilization) and the properties of the reaction liquid. Any plastic materials can be used that are compatible with regard to temperature stability and chemical resistance with the pretreatment and the properties of the reaction liquid and that can be connected to each other by suitable technologies.

The insert may also be one piece, same as the shapes of air balloons, as an inflatable plastic part. In addition it is possible to use the equipment not only as an insert for culture vessels, but to form the walls and the geometry of a culture vessel with the unfoldable or inflatable equipment. Thus results an inflatable or unfoldable culture vessel composed of polymers, which shows the properties of the equipment according to the invention. In this way, inserts or complete culture vessels having volumes from 2 to 20,000 ml can be produced according to the invention.

As a culture vessel, a 1,000 ml Erlenmeyer flask having a reaction volume of 500 ml is used. In the cover cap of the flask (Kapsenberg cap), corresponding holes are drilled for passing the supply lines to the equipment according to the invention, the supply lines are introduced and then tightly sealed with glue. The flask is filled up with the reaction liquid, the equipment is inserted in the not inflated condition through the cover opening into the culture vessel. Then, the flask is sealed with the cap. If the reaction is intended to take place under sterile conditions, a sterilizable air filter is placed on the aeration line (PL in) and the off gas out line (off gas out), and the other supply and discharge lines of the equipment as well as the probe armature are sealed, and the complete vessel is sterilized in the autoclave. Subsequently, the flask is inoculated by addition of a pure culture of the microorganism to be cultivated. The culture vessel is installed in a shaking equipment. According to the invention, the eddy current breakers are inflated with air through the inlet opening Pkin and take their predetermined shape in the culture vessel. The inlet and outlet openings of the eddy current breakers are then sealed, so that the inflated condition is maintained. At the sterile filter of the aeration section is connected an aeration controlled by a flow meter. By means of the sampling system, now an aliquot of the reaction liquid can be taken, e.g. by means of a disposable syringe, for external analysis. To the off air section can be connected an analyzer for the analysis of $CO_2$ and $O_2$ in the off air. At the dosing sections are connected dosing pumps for process reagents, such as lye, anti-foam agent or substrate. Into the probe armature is introduced under sterile conditions a pH electrode, e.g. type Orion pH 9126, previously cold sterilized in sodium lye. The pH probe is sealed by O-rings against the reaction liquid, so that only the diaphragm of the probe necessary for the pH measurement is in contact with the reaction liquid. Then the probe is connected to a pH-measuring device. Subsequently, the biological or biochemical reaction is performed under culture-specific conditions. During the cultivation, the equipment according to the invention permits now the execution of a fermentation, which is comparable, with regard to process conditions, to a high-sophisticated fermenter and in addition makes possible the recording, control and calculation of the following measurement values:

TABLE 1

| Measurement value and designation Culture vessel | Equipment acc. to invention | Standard |
|---|---|---|
| On-line measurement values (i.e. continuously measured). | | |
| pH value | yes | no |
| $O_2$ content in culture vessel | yes | no |
| $CO_2$ content in culture vessel | yes | no |
| Substrate dosage | yes | no |
| Lye dosage | yes | no |
| Anti-foam agent dosage | yes | no |
| Temperature (by pH probe) | yes | no |
| Aeration rate | yes | no |

TABLE 1-continued

| Measurement value and designation Culture vessel | Equipment acc. to invention | Standard |
|---|---|---|
| Off-line measurement values (i.e. determined from aliquots). | | |
| Shaking frequency | yes | yes* |
| Biomass | yes | yes* |
| Growth rate | yes | yes* |
| Composition of medium | yes | yes* |
| Concentration of product | yes | yes* |
| Parameters calculated from on-line and off-line values. | | |
| Oxygen feeding rate | yes | no |
| $CO_2$ production rate | yes | no |
| Respiration coefficient | yes | no |
| Substance transfer coeff. KLA | yes | no |
| Substrate consumpt./time unit | yes | no |
| Dosages/time unit | yes | no |
| Production and consumption per organism | yes | no |

*Only possible with removal of the culture vessel from the shaker, opening the device in suitable environment, sampling. I.e. the reaction is interrupted for this period of time.

The calculation formulas are sufficiently described in the respective literature. In particular the parameters measured on-line and the parameters calculated therefrom are an essential condition for a comparability of the results in the culture vessel to the results of the later production fermenters. According to the invention the construction of the equipment does not only permit the determination of these parameters, but makes possible, because of its construction, to achieve these parameters in orders of magnitude in a simple culture vessel, as they will later be present in the production fermenter. The relative substance transfer coefficient KLA represents for instance one of the most important comparison and scale-up parameters for reactors. The larger the KLA value is, the larger the product of gas exchange area A and oxygen transfer coefficient KL is. If this value is held constant in different reactors, the supply and discharge of gases to and from the reaction liquid and thus the reactors are comparable. The condition for this is that all reactors to be compared can achieve these KLA values. For short and efficient processes, high KLA values are desired, since these make possible high substance exchange rates and thus production yields. If the KLA values of different culture vessels and reactors are compared, then will result, dependent from the shaking frequency and the aeration rate, the following ranges (relative comparison):

List 2

| Erlenmeyer flask without chicanes | KLA 1 to 3% |
| Erlenmeyer flask with chicanes | KLA 1 to 6% |
| Aerated culture bottle | KLA 1 to 30% |
| 1 liter fermenter | KLA 1 to 800% |
| 1 $m^3$ fermenter | KLA 1 to 600% |
| Equipment according to the invention in Erlenmeyer flask | KLA 1 to 800% |

Analogous comparisons are achieved for other parameters, such as oxygen feeding rate or $CO_2$ discharge rate, with the equipment according to the invention. Compared to prior art, this thus permits optimum reaction conditions, as they will later exist in the production scale, and therefore a substantial increase of efficiency and cost savings in the sector of the method development for biological or biochemical three-phase systems.

Example of Execution 1

The equipment according to the invention is made from polypropylene film having a thickness of 0.5 mm. Along the lines according to the diagrammatical drawing 1, glue (e.g. UHU endfest. plus 300, 2 components epoxy resin glue) is uniformly applied to one cut piece, and then the other cut piece is precisely placed on top. Care has to be taken that the inlet and outlet openings of the dosing ducts are not glued, and that the borders of the inflatable part are precisely and tightly glued. After a drying time of 12 hours, the lower part of the fixing ring can be glued on. Equally, the two traverses (not inflatable in this cut pattern) are glued in, and the dosing ducts for aeration, dosing sections and the two eyelets for the probe armature are glued on the traverses. After another drying time of 12 hours, the equipment is ready for use. Specialized manufacturers can produce the equipment according to the invention as one piece as a plastic body formable with gas. As the culture vessel is used a 1,000 ml Erlenmeyer flask (narrow neck) with Kapsenberg cap. In the cap are drilled passage openings for the respective supply lines of the equipment according to the diagrammatical drawing 1, the respective ducts are introduced through the cap and tightly glued in with glue (e.g. UHU endfest. plus 300, 2 components epoxy resin glue). After a drying time of 12 hours, the equipment is, after filling 500 ml medium into the culture vessel, inserted in the not inflated condition into the culture vessel, and all supply lines are sealed with hose clamps. After mounting the cap, the culture vessel can be sterilized in the autoclave. For passing the ducts through, an adapter or a coupling piece may be provided in the cap. As a reference culture vessel, an Erlenmeyer flask without the equipment according to the invention and also without chicanes (Ref. 1), and an Erlenmeyer flask with chicanes, however without the equipment according to the invention (Ref. 2) is used. Both are also filled with 500 ml medium, sealed with a cap and sterilized in the autoclave.

Composition of the Medium

| | |
|---|---|
| Yeast extract for the microbiology | 12 g/l |
| Glucose for the microbiology | 10 g/l |
| Ammonium sulfate | 1.5 g/l |
| Common salt | 0.1 molar |
| Magnesium chloride | 0.5 g/l |
| Potassium phosphate buffer solvent | 0.1 molar, pH 7.2 as |
| Olive oil, extravirgine | 1 ml/l |

The components of the medium are obtainable from the usual specialist shops in identical quality. The components glucose and magnesium chloride are separately sterilized as suitable aliquots and then added under sterile conditions.

After the sterilization and cooling-down of the three culture vessels, the inoculation with a pure culture of the microorganism with one milliliter each is performed under sterile conditions. The pure culture was produced from a tube with *E. coli*, K12, obtainable from the German culture collection (DSM Hannover), and cultivation of the contents of this tube in 10 ml standard 1 medium (Merck Darmstadt) at 37° C. over 12 hours under sterile conditions. The optical density of the pure culture was at the time of the inoculation 1.2 OD (546 nm).

This example shows the superiority of the equipment according to the invention over the prior art in a three-phase system with turbulent mixing compared to 2-phase systems. Therefore, the dosing sections and the off air section were not used in this example.

The equipment according to the invention was inflated with air, 0.5 bar, through the port Pkin, until the final shape was achieved, and the port was sealed with a hose clamp, in order to maintain the pressure and thus the shape. All three culture vessels were placed in a shaker (B. Braun CERTOMAT BS-T); the equipment according to the invention was coupled at the port PLin with an aeration unit (inlet pressure 0.5 bar, air flow 5 liters/h) and continuously aerated. The three culture vessels were cultivated for 16 hours at 37° C. and a shaking frequency of 250 rpm. For determining the growth of the culture (and thus the efficiency of the system), hourly an aliquot of the culture was taken from the culture, and the optical density (OD) was determined at 546 nm with a photometer. Beginning from OD=1.0, corresponding dilutions have to be performed, in order to compensate nonlinearities of the photometer.

Figure 3:
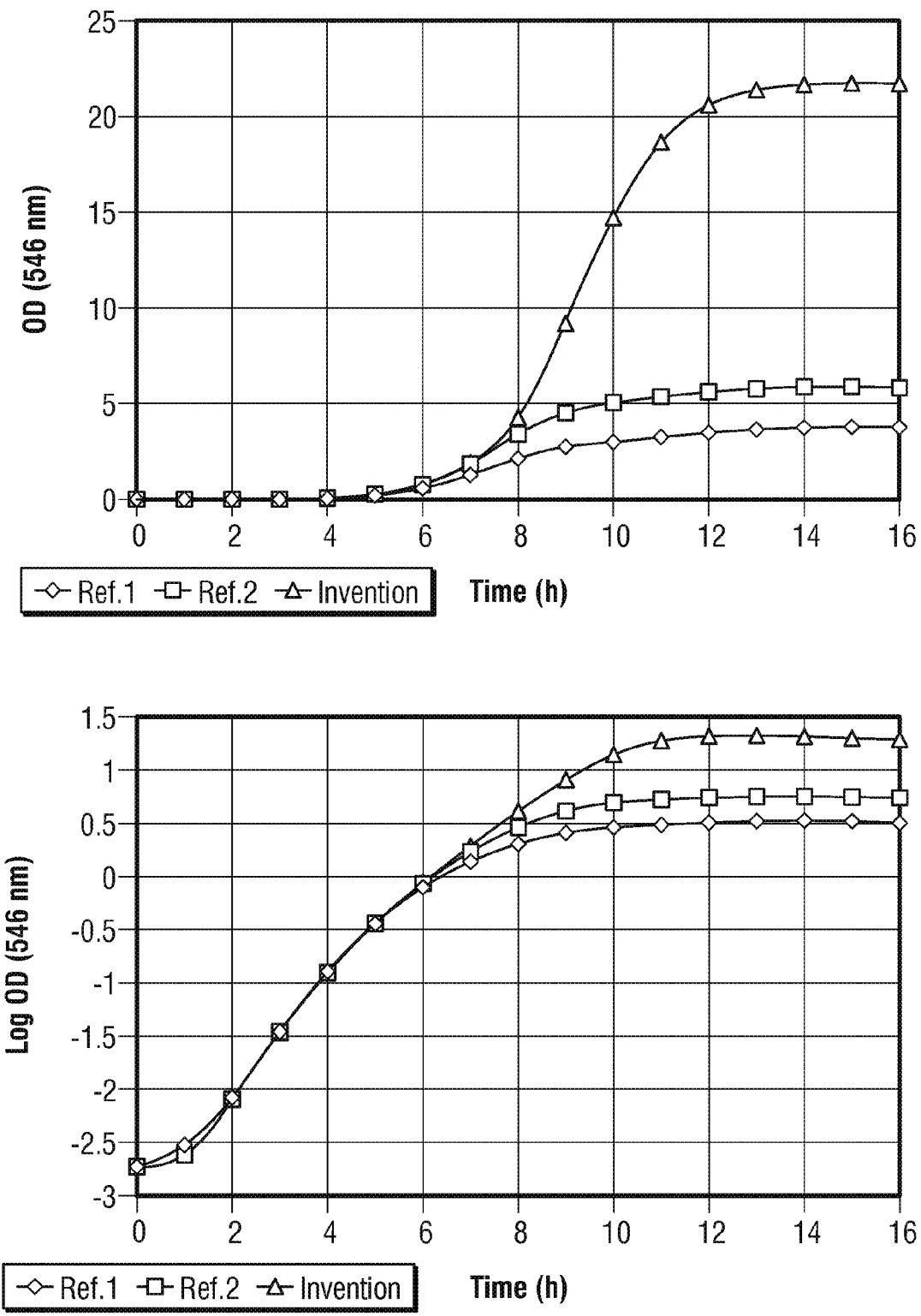
FIG. 3 shows the growth of the cultivated microorganisms in a bioreactor according to the invention with the OD values in a logarithmic scale.

Table 2 and FIG. 3 show the clearly better growth of the cultivated microorganisms in a bioreactor according to the invention. In FIG. 3 are shown the OD values in a logarithmic scale (see also Table 2). The invention achieves compared to Ref. 1 a 5.7 times better OD value, and compared to Ref. 2 a 3.7 times better OD value. Since the optical density directly represents the growth rate of the organism, and thus indirectly its substance exchange rate, it clearly shows as a measurable parameter the increase of efficiency achieved by the invention.

Example of Execution 2

The manufacture of the equipment according to the invention is performed in an analogous manner to example 1. As the culture vessel is used an Erlenmeyer flask (narrow neck) with Kapsenberg flap. In the cap are drilled passage openings for the respective supply lines of the equipment according to diagrammatical drawing 1, the respective ducts are introduced through the cap and tightly glued in with glue (e.g. UHU endfest plus 300, 2 components epoxy resin glue). After a drying time of 12 hours, the equipment is, after filling 450 ml medium into the culture vessel, inserted in the not inflated condition into the culture vessel, and all supply lines are sealed with hose clamps. After mounting the cap and introducing a sterilizable, calibrated pH electrode into the probe armature, the culture vessel can be sterilized in the autoclave. As a reference (Ref. 3) a mini-fermenter type LAB-FORS of the company Infors is used. This equally represents a three-phase system with built-in chicanes, is however not shaken, but is provided with a stirring mechanism. In contrast to the culture vessels described in example 1, it represents the smallest possible unit of a fermenter. The data obtained with this system can be used for a scale-up of the process into the production scale. By means of this example, it is intended to show that the equipment according to the invention is capable, when used in simple culture vessels, to achieve and to exceed the performance of this high-sophisticated fermenter system. The fermentation vessel is filled with 450 ml medium and sterilized according to manufacturer's instructions in the autoclave.

Composition of the Medium

| | |
|---|---|
| Yeast extract for the microbiology | 20 g/l |
| Ammonium sulfate | 1.5 g/l |
| Common salt | 0.1 molar |
| Magnesium chloride | 0.5 g/l |
| Potassium phosphate buffer solvent | 0.1 molar, pH 7.2 as |

-continued

| Anti-foam agent (Silicon oil Dow Corning) | 1 ml/l |
|---|---|

| KLA value reference culture Ref. 3 | 210 ± 24 (l/h) |
|---|---|
| KLA value invention | 218 ± 27 (l/h) |

The components of the medium are obtainable from the usual specialist shops in identical quality. The component magnesium chloride is separately sterilized as a suitable aliquot and then added under sterile conditions. As substrate feed serves glucose (20 g in 50 ml), as lye feed serves 25% ammonia solution (ammonia addition under sterile conditions after the sterilization of the feed vessel), contents 50 ml, and as anti-foam feed serves 10% silicon oil (Dow Corning), contents 50 ml.

After the sterilization and cooling-down of the two culture vessels, the inoculation with a pure culture of the microorganism with one milliliter each is performed under sterile conditions. The pure culture was produced from a tube with E. coli, K12, obtainable from the German culture collection (DSM Hannover), and cultivation of the contents of this tube in 10 ml standard 1 medium (Merck Darmstadt) at 37° C. over 12 hours under sterile conditions. The optical density of the pure culture was at the time of the inoculation 1.36 OD (546 nm). The equipment according to the invention is prepared, as described in example 1, and placed in a shaker (B. Braun CERTOMAT BS-T), coupled at the port PLin with an aeration unit (inlet pressure 1 bar, air flow 15 liters/h) and continuously aerated. The pH electrode is connected to a pH measuring and controlling device. To the dosing sections are connected the substrate feed, the lye feed and the anti-foam feed. To the off air line off gas out is connected a measuring device for determining the $O_2$ and $CO_2$ content of the off air, in order to be able to calculate the KLA value of the system. The shaking frequency for this experiment is 350 rpm. The vessel is tempered to 37° C. The reference fermenter Ref. 3 is connected according to manufacturer's instructions to the pH measuring and controlling equipment, the substrate dosage, the lye dosage and anti-foam dosage and at the air off section further to an $O_2$ and $CO_2$ measuring equipment. The speed of the stirring mechanism is 600 rpm, the air flow for aeration also 15 l/h. The fermenter is tempered to 37° C.

Dosage Parameters for both Approaches
Substrate dosage continuous with 2.5 ml/h (1 g glucose per h)
Lye dosage for controlling the pH value, desired pH>7.0
Anti-foam dosage only when needed, i.e. over-foaming of the culture Both approaches were cultivated for 20 hours each. For determining the growth of the culture (and thus the efficiency of the system), hourly an aliquot of the culture was taken from the culture, and the optical density (OD) was determined at 546 nm with a photometer. Beginning from OD=1.0, corresponding dilutions have to be performed, in order to compensate nonlinearities of the photometer. The KLA values were calculated following the dynamic method (Bandyopadhyay, B., Humphrey, A., and Taguchi, H., 1967, Biotechnol. and Bioeng. 9, 533).

Figure 4:
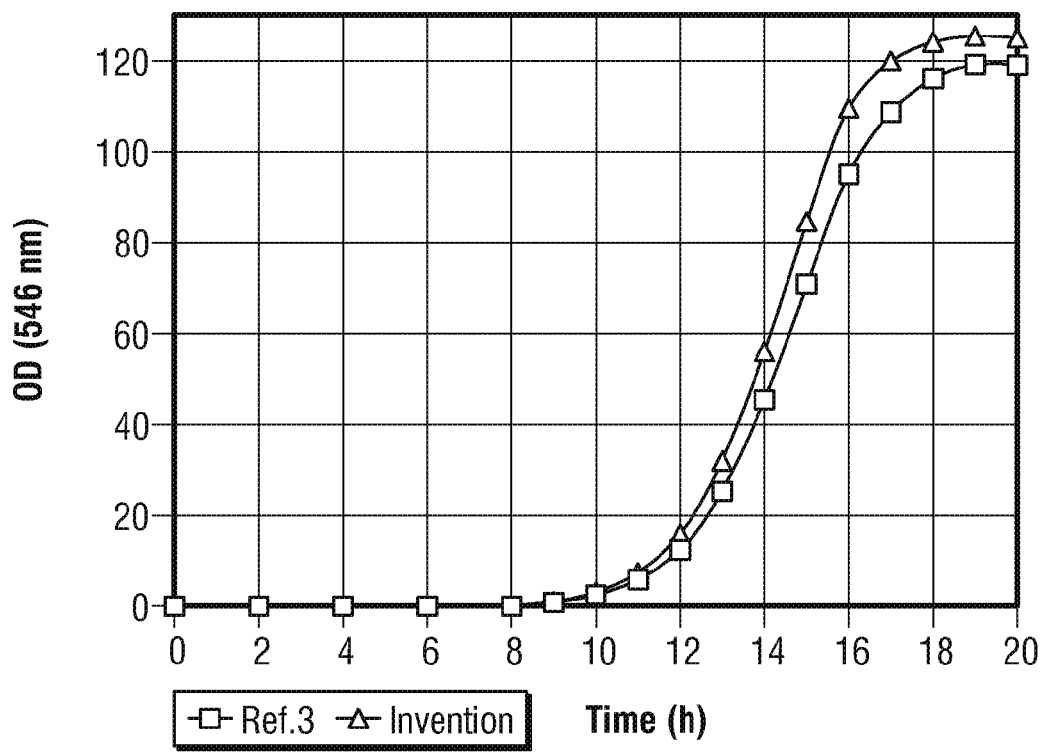
FIG. 4 shows the comparability or superiority of the equipment according to the invention over the prior art fermenters with the OD values in a logarithmic scale.
Figure 4:
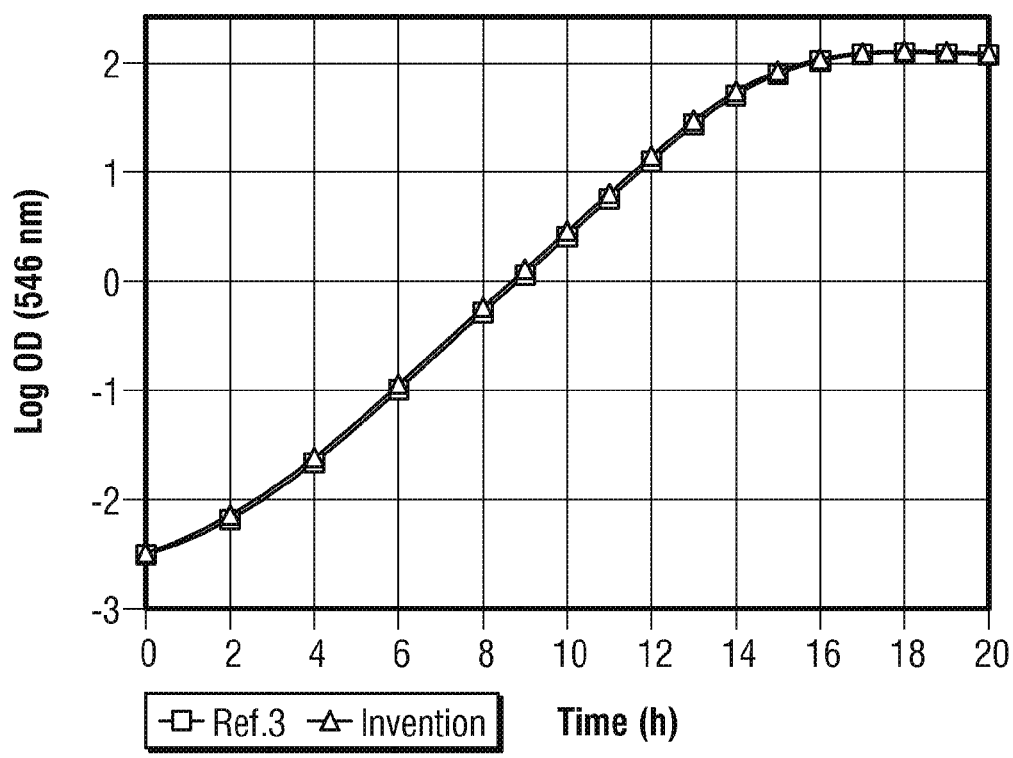

Table 3 and FIG. 4 clearly show the comparability or superiority of the equipment according to the invention over the prior art fermenters. In Table 3a and FIG. 4a are shown the OD values in a logarithmic scale. Same as in example 1, the optical density is used as a measure for the efficiency of the reactor. A comparison of the dynamically determined KLA values very well shows the comparability of the process engineering and biological conditions between the two approaches.

The growth curves and absolute OD values are practically identical (slightly higher for the invention), which proves an excellent comparability of the two systems, and thus shows that the equipment according to the invention is far superior to conventional culture vessels in use up to now, and is at least comparable to high-value fermentation systems.

The invention can be combined with the following features, namely a method and a device for producing a carrier fluid, which simultaneously can be used for the aeration of the culture vessel. To the carrier fluid can be admixed the fluids to be dosed in a quantitative and defined manner. Without using pumps and other expensive parts, thus defined and controlled conditions can be generated in the culture vessel in the reaction liquid and in the atmosphere of the vessel, simultaneously the properties of the dosed fluids being used in an optimum manner. Particularly well suited is the invention for the parallel operation of several culture vessels. The present invention is applicable in all sectors, where in culture vessels biological or biochemical reactions are performed, particularly in the field biotechnology, food technology and environmental protection.

TABLE 2

OD of the three culture vessels

| Time (h) | Ref. 1 | Ref. 2 | Invent. |
|---|---|---|---|
| 0 | 0.002 | 0.002 | 0.002 |
| 1 | 0.003 | 0.002 | 0.003 |
| 2 | 0.01 | 0.009 | 0.01 |
| 3 | 0.038 | 0.042 | 0.04 |
| 4 | 0.16 | 0.146 | 0.15 |
| 5 | 0.41 | 0.48 | 0.36 |
| 6 | 0.76 | 0.87 | 0.86 |
| 7 | 1.31 | 1.53 | 1.89 |
| 8 | 2.37 | 3.87 | 4.56 |
| 9 | 2.82 | 4.65 | 9.65 |
| 10 | 3.12 | 5.32 | 15.45 |
| 11 | 3.34 | 5.56 | 19.46 |
| 12 | 3.67 | 5.87 | 20.8 |
| 13 | 3.72 | 6.01 | 21.6 |
| 14 | 3.85 | 5.98 | 21.86 |
| 15 | 3.82 | 5.94 | 21.76 |
| 16 | 3.84 | 5.97 | 21.89 |

TABLE 2a log OD of the three culture vessels

| Time (h) | Ref. 1 | Ref. 2 | Invent. |
|---|---|---|---|
| 0 | 2.698970004 | 2.698970004 | 2.698970004 |
| 1 | 2.522878745 | 2.698970004 | 2.522878745 |
| 2 | −2 | −2.045757491 | −2 |
| 3 | −1.420216403 | −1.37675071 | −1.397940009 |
| 4 | −0.79588001 | −0.83564714 | −0.82390874 |
| 5 | −0.387216143 | −0.318758763 | −0.443697499 |
| 6 | −0.119186408 | −0.060480747 | −0.065501549 |
| 7 | 0.117271296 | 0.184691431 | 0.276461804 |
| 8 | 0.374748346 | 0.587710965 | 0.658964843 |
| 9 | 0.450249108 | 0.667452953 | 0.984527313 |
| 10 | 0.494154594 | 0.725911632 | 1.188928484 |
| 11 | 0.523746467 | 0.745074792 | 1.289142836 |
| 12 | 0.564666064 | 0.768638101 | 1.318063335 |
| 13 | 0.57054294 | 0.778874472 | 1.334453751 |
| 14 | 0.58546073 | 0.776701184 | 1.339650158 |

TABLE 2a-continued log OD of the three culture vessels

| Time (h) | Ref. 1 | Ref. 2 | Invent. |
|---|---|---|---|
| 15 | 0.582063363 | 0.773786445 | 1.337658891 |
| 16 | 0.584331224 | 0.775974331 | 1.340245762 |

TABLE 3

OD of the two cultures

| Time (h) | Ref. 3 | Invent. |
|---|---|---|
| 0 | 0.004 | 0.003 |
| 2 | 0.006 | 0.007 |
| 4 | 0.026 | 0.023 |
| 6 | 0.15 | 0.14 |
| 8 | 0.67 | 0.56 |
| 9 | 1.38 | 1.58 |
| 10 | 2.98 | 3.45 |
| 11 | 6.12 | 7.23 |
| 12 | 12.56 | 16.41 |
| 13 | 24.1 | 31.8 |
| 14 | 46.2 | 58.7 |
| 15 | 75.8 | 86.9 |
| 16 | 96.4 | 112.8 |
| 17 | 107.8 | 119.8 |
| 18 | 116.7 | 124.7 |
| 19 | 121.5 | 126.8 |
| 20 | 118.9 | 126.1 |

TABLE 3a log OD of the two cultures

| Time (h) | Ref. 3 | Invent. |
|---|---|---|
| 0 | −2.397940009 | −2.522878745 |
| 2 | −2.22184875 | −2.15490196 |
| 4 | −1.585026652 | −1.638272164 |
| 6 | −0.823908741 | −0.853871964 |
| 8 | −0.173925197 | −0.251811973 |
| 9 | 0.139879086 | 0.198657087 |
| 10 | 0.474216264 | 0.537819095 |
| 11 | 0.786751422 | 0.859138297 |
| 12 | 1.0989899639 | 1.215108581 |
| 13 | 1.382017043 | 1.50242712 |
| 14 | 1.66461976 | 1.768638101 |
| 15 | 1.879669206 | 1.939019776 |
| 16 | 1.984077034 | 2.0523091 |
| 17 | 2.032618761 | 2.078456818 |
| 18 | 2.067070856 | 2.095866453 |
| 19 | 2.084576278 | 2.103119254 |
| 20 | 2.075181855 | 2.100715087 |

The method is characterized by that the fluid to be dosed or the fluids to be dosed are admixed to one or several carrier and transport fluids in a defined concentration, and that this carrier fluid or these carrier fluids are fed to the culture vessel in a defined amount and/or defined time units either into the reaction medium or the headspace.

The device is characterized by devices for admixing one or more fluids to be dosed to one or more carrier fluids and the supply to one or more culture vessels, as they will be described in the following examples and patent claims.

As an example, in the following the description of the individual modules and properties according to the invention is given with reference to a 1,000 ml culture vessel with a 500 ml liquid volume. It is specifically emphasized that the numbers (in particular the relative statements) can be adjusted to culture vessels having volumes of 1 ml to 50 m$^3$, the cross sections of the nozzles and dosing sections respectively having to be adjusted.

a) Gas as the Transport Medium of the Device

The module gas supply of the device is composed of the following essential components (drawing 1):
pressure gas inlet
three-way valve DV1 or inlet and outlet valve
gas container B1
gas filter F1
pressure compensation duct DG1

The pressure gas inlet with an input over-pressure compared to the culture vessel of 0.1 to 10 bars, preferably 0.2 to 1 bar, in particular 0.5 bar, is connected via a pressure-resistant hose, internal diameter 0.5 to 8 mm, preferably 0.5 to 2 mm, in particular 1 mm, to the three-way valve DV1 (see drawing 1). The valve DV1 is arranged such that the gas container B1 with a container volume of 1 to 40%, preferably 1 to 10%, in particular 5%, of the liquid volume in the culture vessel, is filled with pressurized air or another gas. A built-in piston can vary the filling volume of the gas container from 0 to 100% of the container volume. After achieving the pressure compensation, the valve DV1 is changed to the other position, gas container—culture vessel. By the pressure compensation, a gas flows toward the culture vessel is generated, and said gas flow can be conducted behind an optional gas filter through the modules described below and finally flows out in the headspace or the reaction liquid of the culture vessel. The capillary for the pressure compensation branching off behind the three-way valve DV1 provides for an equalized pressure between the gas supply and the modules liquid feed. At the output of the module gas supply, a filter may be provided for the filtration of the transport medium. The culture vessel is supplied by this device according to the invention discontinuously in a simple way with defined and thus quantifiable "gas portions". The smaller the container volume and the higher the clock rate of the valve is, the more this discontinuous gas flow approximates to a continuous gas flow. In the following table, the container volume is 5% of the liquid volume of the reaction liquid (example 25 ml container volume, 500 ml reaction liquid volume) and the aeration rate VF the quotient of gas volume/h divided by volume reaction liquid.

TABLE 1

| Clock rate Valve/min | Gas flow/min in % liquid volume | VF (l/h) |
|---|---|---|
| 0 | 0% | 0 |
| 1 | 5% | 3 |
| 2 | 10% | 6 |
| 5 | 25% | 15 |
| 10 | 50% | 30 |
| 15 | 75% | 45 |
| 20 | 100% | 60 |
| 25 | 125% | 75 |
| 50 | 250% | 150 |

For aerobic, biological or (bio)chemical reactions, the VF values are usually between 5 and 60 (l/h). This can easily be achieved with the present module according to the invention in a nearly "continuous" gas flow, complicated mechanical or electronic flow measurements and regulators not being required. Essential for an optimum and continuous gas supply of cultures of microorganisms with optimum use of the gas is the so-called "gas hold-up", i.e. the hold-up time of the gas bubbles in the reaction liquid, whereas the gas exchange can take place at the border face between gas bubble and liquid by diffusion. An optimum use of the gas with simultaneous optimum aeration rate is achieved, when the "gas gold-up" is equal to the clock rate of the valve DV1. There is always a dosage of gas, when the gas bubbles disappear from the liquid.

A variation of the amount of passed-through gas can be achieved by the variable volume of the gas container. Furthermore, the structure according to the invention of the module reduces the tendency to foam generation, since there is dosed always that amount only of gas, which is necessary for an optimum supply to the culture.

b) Liquid as the Transport Medium

In lieu of the module gas supply, liquid can be used as the transport medium. In this case, the module gas supply is replaced by a controlled liquid pump, which is either connected by a suction line to the reaction liquid in the culture vessel and circulates the liquid or sucks it in from an own storage vessel (drawing 2). The module driving pump is composed of the following essential components:

liquid pump.

suction line.

pressure line toward the culture vessel.

filter (optional).

The use of liquid as the transport medium is then useful, if the reaction liquid is to be enriched efficiently, but under avoidance of gas bubbles with gases, e.g. $CO_2$ dosage in cell culture media or dosage of minimum amounts of substances. The dosage of catalyzers or the dosage of biological active ingredients can for instance be mentioned here. Active ingredients are in most cases extremely expensive and are stable for long times in a concentrated form only. According to the invention, they are dosed with liquid modules in smallest amounts (see below) and in arbitrary combinations.

c) Module Liquid Feed

The module liquid feed is composed of the following essential components (drawing 1):

storage container liquid.

line for pressure compensation, branched-off from the capillary for pressure compensation.

supply line to the clock valve and the Venturi nozzle.

clock valve.

Venturi nozzle.

The liquid feed is filled with a liquid to be dosed to the reaction liquid in the culture vessel, and a remaining volume of gas of at least 2% of the volume of the feed must be present for the pressure compensation. If the transport medium is a liquid, there needs not to be the remaining volume of the gas and the pressure compensation by capillaries (drawing 2). Instead, the feed can be aerated with atmospheric external pressure for preventing an underpressure. The liquid feed can be installed in any position, suspended, standing, lying with regard to the device, and the line for the pressure compensation should terminate in the present gas volume. The liquid feed has, compared to the liquid volume of the reaction liquid, a volume of 0.5 to 50%, preferably 5%. It is connected by a line to the clock valve V1, and the latter to the Venturi nozzle VD1. If the module gas supply or driving pump delivers a flow of transport medium via the Venturi nozzle, at the side inlet of the nozzle an underpressure will be generated, compared to the otherwise pressure-compensated system. With simultaneous opening of the clock valve V1, thus liquid is sucked in from the liquid feed toward the gas flow in the nozzle. The sucked-in amount of liquid correlates with the following parameters:

TABLE 2 nozzle dimensions.
pressure and gas flow through the nozzle.
cross-sections of the supply line and of the clock valve.
viscosity of the liquid.
temperature.

and can therefore be quantitatively and reproducibly calibrated. Therefore, it is possible to perform a quantitative dosage of liquid aliquots to the transport medium based on the cycle time of the valve V1 only at constant parameters according to Table 2. In the outlet of the nozzle, the sucked-in liquid and the transport medium are homogeneously mixed. Between the module gas supply or module drive (drawing 5 and 6) and the module culture vessel, several modules liquid feed, preferably 4 modules, can be provided. The arrangement can be parallel (preferred) or in series. In this way it is possible to quantitatively dose into the transport medium simultaneously no liquid to several different liquids, to combine them in any amounts and to homogeneously mix them before the inlet into the culture vessel. In biological cultures, beside the titration of the pH value with acids and lyes and the addition of means for foam abatement, in particular so-called "fed batch" methods are usual. Herein, one or several substrates, e.g. carbon or nitrogen source, are dosed to the culture in a controlled manner. The present device permits in a very simple way to vary the composition of the liquid dosage. For instance, by the variation of the cycle time only, substrate gradients can be established in dependence of the time or of culture-specific control parameters, or additional nutrients can be admixed, such as growth factors, minerals or vitamins from further liquid modules.

d) Module Dosage Feed for Gases

Figure 7:
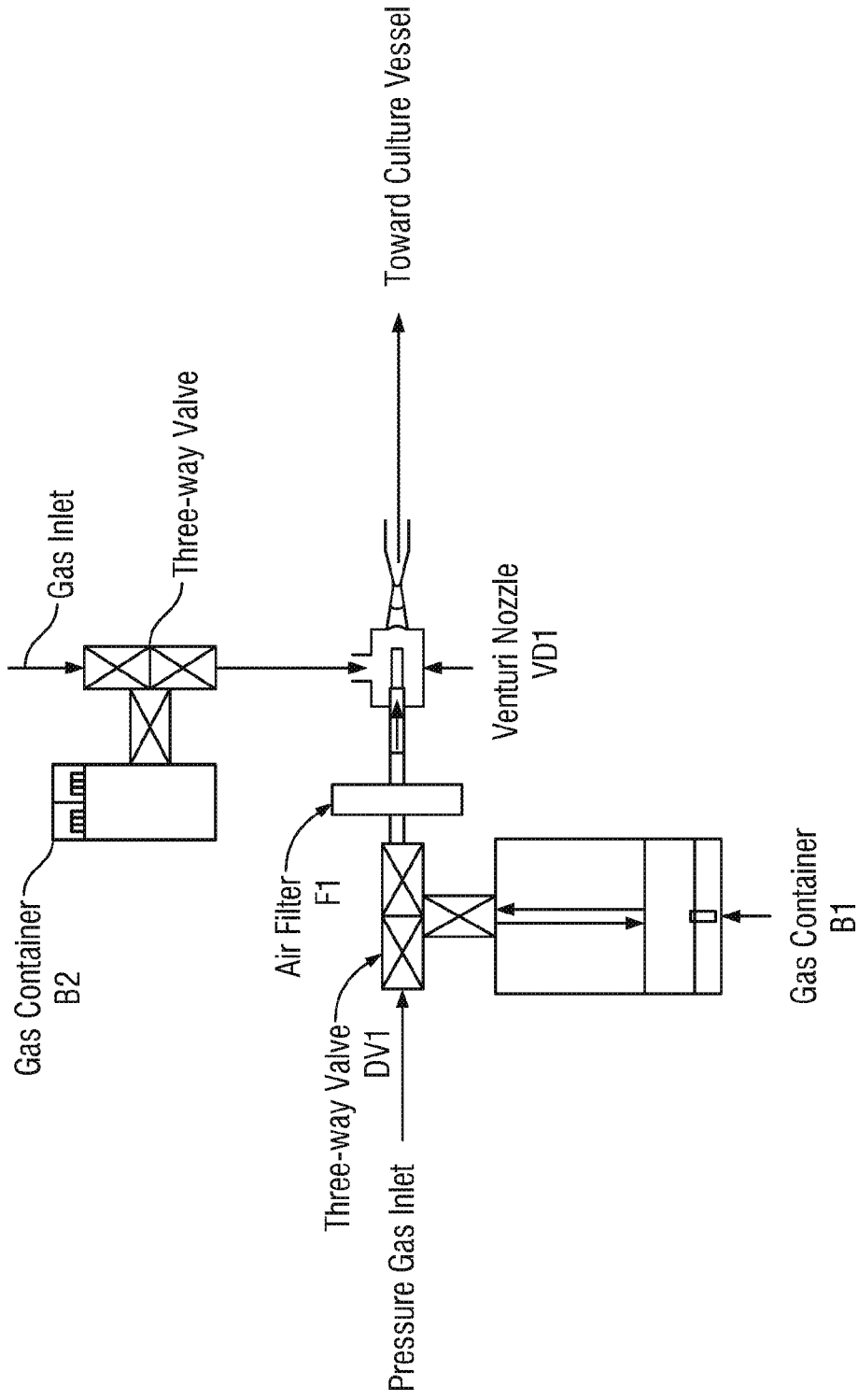
FIGS. 7 and 8 show the module dosage feed for gases which is composed of the following essential components: gas container B2, adjustable by a piston in the filling volume, gas inlet and three-way valve.
Figure 8:
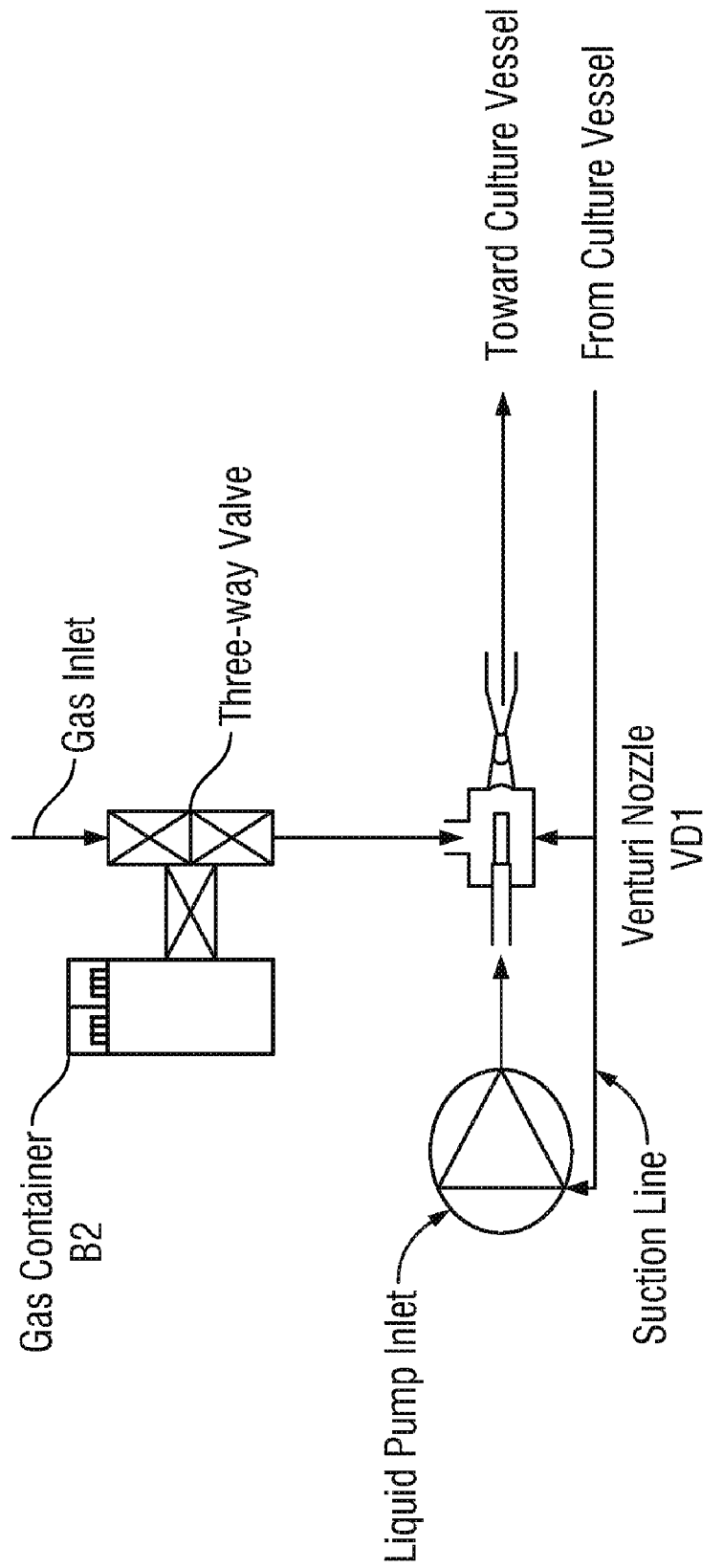

The module dosage feed for gases (FIGS. 7 and 8) is composed of the following essential components:

gas container B2, adjustable by a piston in the filling volume.

gas inlet.

three-way valve.

The three-way valve is installed between the gas inlet and the gas container B2. The container fills up with gas, and the filling volume can be varied by the built-in piston, is thus however quantitatively known. If now a gas dosage is to be made, the three-way valve is switched over for a defined cycle time toward the Venturi nozzle, and it should be made sure that there is an underpressure at the nozzle generated by the transport medium. With known inlet pressure at the gas inlet, filling volume of the gas container and cycle time of the three-way valve, thus a quantitative gas dosage can be achieved. Between the module gas supply or module drive (drawing 1 and 2) and the module culture vessel, several modules gas dosage, preferably 2 modules, can be provided. The arrangement can be parallel (preferred) or in series. In this way it is possible to quantitatively dose into the transport medium simultaneously no gas to several different gases, to combine them in any amounts and to homogeneously mix them before the inlet into the culture vessel. The gas modules can be used in lieu of or in any combination with the liquid modules. In biological cultures, frequently $CO_2$ is employed for regulating the pH value, which can easily and quantitatively be dosed with this module under avoidance of gas bubbles in the reaction liquid. Furthermore, by the gas dosage, an artificial atmosphere can be created and controlled in the culture vessel, what is advantageous for biological cultures. Here can be named for instance the culture of plant cells, which prefer a higher $CO_2$ concentration (as a substrate) or the breeding of anaerobic organisms in a nitrogen or sulfur atmosphere.

e) Module Culture Vessel

The module culture vessel is composed of the following essential components:
- culture vessel KG1, filled with the reaction liquid and gas space thereabove (headspace) and cover of the vessel.
- supply line for the transport medium.
- inlet valve EV1 with supply line into the headspace of the culture vessel.
- inlet valve EV2 with supply line into the reaction liquid.
- ventilation nozzle BD1 in the reaction liquid.
- ejector nozzle AD1 in the headspace of the culture vessel.

By the inlet valves provided at the cover of the culture vessel, it is possible to select whether the transport medium is to be dosed into the air space of the culture vessel (headspace) or into the reaction liquid. The inlet valve EV1 to the headspace leads to an atomization nozzle AD1 installed in the air space, which again generates an atomization of the transport medium. The complete, atomized transport medium and the dosages go uniformly down on the surface of the reaction liquid. This fine distribution causes a quick mixture of the transport medium and the dosages with the reaction liquid and can lead to a more efficient use of the dosed liquid. The efficiency of anti-foam agents, which are dosed in this way, can hereby be increased 10 times, thus the consumption can correspondingly be minimized. Further, it is possible to use a gas flow only without dosed liquid for foam abatement. The foam is simply "blown down" by the gas flow. Frequently, this effect is already sufficient for the foam abatement, without the necessity of subsequently dosing anti-foam agent. The avoidance of anti-foam agents in biological processes is the most important aim, since they could have negative effects on the culture itself and on the later purification process, and are biologically poorly degradable and can therefore not easily be disposed of. Headspace dosages in the above manner are mainly used, if an aeration of the surface of the reaction liquid is desired, e.g. for anaerobic cultures or if liquids are dosed, which should have a fast effect on the reaction liquid. As an example, here is mentioned the titration of the pH value with acids or lyes, and the foam abatement in the manner described above. The inlet valve EV2 leads to a Venturi nozzle BD1 arranged in the reaction liquid. The transport medium (and the dosages) flows through the ventilation nozzle BD1 into the reaction liquid. Reaction liquid is sucked in at the lateral inlet of the nozzle because of the generated underpressure, said reaction liquid being effectively mixed in the outlet section of the nozzle. If the microorganisms (e.g. tissue cells) are not to be subjected to the shearing forces in the nozzle, the lateral inlet opening can be sealed by a filter membrane. In addition to the mixing effect drastically reducing the mixing times of the reaction liquid, and to the clearly accelerated gas exchange rates, very much smaller air bubbles are generated (with transport medium gas) than with prior art aerations. These smaller bubbles increase the border area available for the gas exchange between air bubble and reaction liquid, that is, they increase the gas exchange rate and remain for a longer time in the reaction liquid than large bubbles, thus increase the "gas hold-up" and therefore again the gas exchange rate. This gas is used in a more effective way, so that, depending from the kind of cultivation, shaking or stirring of the culture vessel is not necessary, if applicable. Furthermore the tendency to foam formation is minimized by smaller bubbles. If in this way aerosols are dosed, e.g. substrates in the gas flow, the shorter mixing times lead to a faster, homogeneous distribution in the reaction liquid. Substrate gradients because of poor mixture can be prevented, the culture is uniformly supplied in the desired manner.

This type of execution has the advantage in that it combines in a suitable way function modules for completely new fields of applications and thus provides a previously expensive and complex technology in a simple, compact device. The use of the device for biotechnical processes under sterile conditions becomes possible. Hereby, sectors become available to control functions, which up to now could not be solved by prior art devices. As an example is mentioned here the novel parallel fermentation of culture vessels, usually up to 16 vessels (Das GIP GmbH, www.dasgip.de), serving for the optimization of media and processes of biological methods. Herein, the effects of different parameters on the result of the culture are intended to be investigated under nearly production conditions, and with regard to measurement and control, the conditions of the production facility would already be desirable, i.e. effective aeration and dosage of different liquids. As mentioned above, such a parallel fermentation would require 96 pumps, 96 regulators and 16 controlled supply sections, and is therefore technically and economically impractical and nonetheless does not meet, even when bubble columns are used as the culture vessel, the measurement and control conditions of a production facility. The trend is to a further miniaturization and increase of the number of culture vessels, in order to obtain in a shorter time more results in a reproducible and quantifiable form (recordable). This is not achievable anymore with prior art devices, however by means of the present invention. The function modules can be produced in any size and can thus be adjusted to the size of the culture vessel, and the volumes of the culture vessels can be between 1 ml and 50 cubic meters. For culture vessels having a liquid volume of 1 ml to 500 ml, the complete device including the liquid and gas feeds and the valve controller can be fixed at the neck of the culture vessel. The data exchange with the control EDP takes place via an infrared interface. There is thus only one supply line to the culture vessel required, consisting of a gas supply line and a power supply. A further miniaturization of the device can take place by that the functional parts and supply lines are etched, cut or molded in corresponding materials, such as steel and plastic materials, and the valve function is achieved by inserted seals operated by pistons, or arbitrary other mini-valves. The device according to the invention can be combined with constructs in the culture vessel, e.g. patent application having the title "Device as a construct for culture vessels for optimized aeration and dosage of shaken or stirred three-phase systems" (file number will be submitted later). By the combination, a high-performance culture vessel is generated, which can reproduce and simulate in a very simple way in a nearly arbitrary scale the complete measurement and control technology and the process parameters of a high-performance fermenter.

Example of Execution

Materials

| Culture vessel: | 1,000 ml Erlenmeyer flask (narrow neck) with Kapsenberg. |
|---|---|
| Composition of the medium: | |
| Yeast extract for the microbiology | 20 g/l |
| Glucose for the microbiology | 1 g/l |
| Ammonium sulfate | 1.5 g/l |

| | |
|---|---|
| Common salt | 0.1 molar |
| Magnesium chloride | 0.5 g/l |
| Potassium phosphate buffer solvent | 0.1 molar, pH 7.2 as |
| Olive oil, extravirgine | 1 ml/l |

Three-way valve DV1: The Lee Company, type LHDA12311115H.
Clock valve V1, V2: The Lee Company, type LFVA 1230210H.
Inlet valve EV1, EV2: The Lee Company, type LFVA 1230210H.
Venturi nozzle VD1, VD2: Spraying Systems, type.
Ventilation nozzle BD1: Spraying Systems, type.
Ejector nozzle AD1: Spraying Systems, type.
Air container B1: Braun Melsungen, disposable syringe 50 ml with Luer Lock.
Air filter F1: Sartorius, disposable sterile filter, 0.2 µm.
Liquid feeds: disposable ampules, 25 ml with flange cap and rubber seal.
Hoses: Teflon hose, 1 mm inner diameter.
Couplings: Luer Lock.
Foam-detection: isolated needle with mass connection to the reaction liquid.
Valve controller: Braun Melsungen DCU3 system.

The components of the medium are obtainable from the usual specialist shops in identical quality. The components glucose and magnesium chloride are separately sterilized as suitable aliquots and then added under sterile conditions. The culture vessel was filled up with 500 ml medium and sterilized in the autoclave. The supply lines to the headspace and to the reaction liquid with the nozzles were guided through a bore in the cover, sealed and equally sterilized together with the vessel. The separation to the device according to the invention was made at the exit of the inlet valves. As liquid feeds served 24 ml glucose solution (100 g/l) and 24 ml anti-foam agent (Dow silicon oil, 10% suspension) each, which are separately sterilized. The device according to the invention is installed, as far as there are no other fixing means provided for the individual components, according to FIG. 5 with Luer Lock fittings and Teflon hoses and fixed on a working panel. The power part between the air filter exit and the exit of the outlet valves as well as the supply and discharge lines of the liquid feed are decontaminated with 10 m soda lye (2 h), and then rinsed with sterile 0.1 m phosphate buffer pH 7.2. After the sterilization and cooling-down of the culture vessel, the inoculation was performed with a pure culture of the microorganism with one milliliter each under sterile conditions. The pure culture was produced from a tube *E. coli*, K12, obtainable from the German culture collection (DSM Hannover), and cultivation of the contents of this tube in 10 ml standard 1 medium (Merck Darmstadt) at 37° C. over 12 hours under sterile conditions. The optical density of the pure culture was at the time of the inoculation 0.9 OD (546 nm). The device was coupled with the inlet valves to the culture vessel and to the module gas supply. To the liquid feed 1 was connected the glucose solution, to the second one the anti-foam agent. The liquid feeds were used in a standing orientation. As a connection for the pressure superimposition, a short disposable injection needle as used, for the liquid removal a long one, which were passed through the rubber seal in a sterile manner. At the pressure air inlet, pressurized air with an overpressure of 0.5 bar was connected. The volume of the gas container was adjusted to 25 ml. The complete device and the culture vessel were tempered to 37° C. in an incubator. The culture vessel was not shaken, since the gas flow alone provided for a sufficient gas supply of the culture. The valves of the device according to the invention were connected to the control unit DCU3 and regulated, as shown in Table 3:

Table 3
Gas Supply
Clock rate 15 fillings and gas flows per minute, corresponds to a VF of 45 or 22.5 air/h, inlet valve EV1 closed, EV2 open, i.e. gas flow into the reaction liquid.
Liquid Feed 1, Substrate
Clock valve V1, open four times per minute for 0.2 seconds, at the same time as the connection of a gas flow to the culture vessel, DV1 open toward the culture vessel, EV2 open, corresponds to a glucose dosage of 1 ml per hour.
Liquid Feed 2, Anti-Foam Agent
Clock valve V2 normally closed. When the transducer needle indicates a foam signal, the following algorithm proceeds: inlet valve EV2 is closed, inlet valve EV1 opened, i.e. headspace aeration start of a timer. If the foam signal of the transducer needle is negative after 8 seconds, the valve EV1 is closed, and the valve EV2 opened, return to standard operation. If the foam signal is still present, then at the same time as every clock signal of the gas supply, the clock valve V2 is opened for 1 second, and so anti-foam agent (18.7 ml/h) is admixed to the air flow of the gas supply. If the foam signal is after another 16 seconds still present, the valve EV2 is in addition opened, in order to supply gas to the culture again. This condition is maintained, until the signal of the transducer needle is negative. Then return to standard operation.

After 24 hours, the cultivation of the microorganisms was stopped, and the optical density (OD) was determined at 546 nm with a photometer. The OD of approx. 90 corresponds to the value to be expected in a high-performance fermenter and demonstrated the capabilities of the device. The substrate feed was completely consumed at this point in time. For the anti-foam agent was measured a consumption of approx. 2 ml, distinctly less than the amount, which a conventional fermenter would have needed for this result (approx. 12 ml, depending from the regulation algorithm).

During the execution of this example, the following could particularly clearly be observed:
  The compact, simple type of execution of the device according to the invention.
  The effectivity of the "pulsed" aeration system in combination with the ventilating nozzle.
  The generated extremely fine gas bubbles.
  The short mixing times of the system.
  The performance of the foam abatement by the structure according to the invention.
  The precise uniform dosage of the liquids.

Once again it is emphasized that these results, which correspond to those of a high-performance fermenter, were achieved without shaking or stirring. On combinations with inserts, by shakers or stirrers, the performance can further be increased.

As a summary, also disclosed is a method for the dosed addition of one or several fluids or fluid mixtures to one or several culture vessels, characterized by a the use of at least one carrier fluid, which is quantitatively, discontinuously taken through a clock valve from a pressurized storage vessel having a defined internal volume.

Further embodiments in any combination by the use of a carrier gas or a carrier gas mixture, by the use of a carrier gas or a carrier gas mixture, by that the fluid(s) to be dosed are admixed to the carrier fluid(s) in a dosed manner through one or several Venturi nozzles, by that the supply to the reaction medium in the culture vessel takes place through a Venturi nozzle for a better mixture, by that a filter or the like at the side inlet of the Venturi nozzle in the reaction medium prevents the ingress of microorganisms into the nozzle, by a supply line to the headspace of the culture vessel, by atomization device such as e.g. an ejector nozzle at the entrance of the headspace, by a commutation of the supply to the culture vessel from the supply to the reaction medium to the supply to the headspace and vice versa, by that the carrier gas or the carrier gas mixture is taken from a gas container under an overpressure, by that the pressure in the gas container during the process is increased again once or several times after one removal or several removals through a supply line, by that they are admixed to the carrier fluid through various Venturi nozzles in series or parallel connection, preferably parallel connection, at the same time or in any order.

Figure 5:
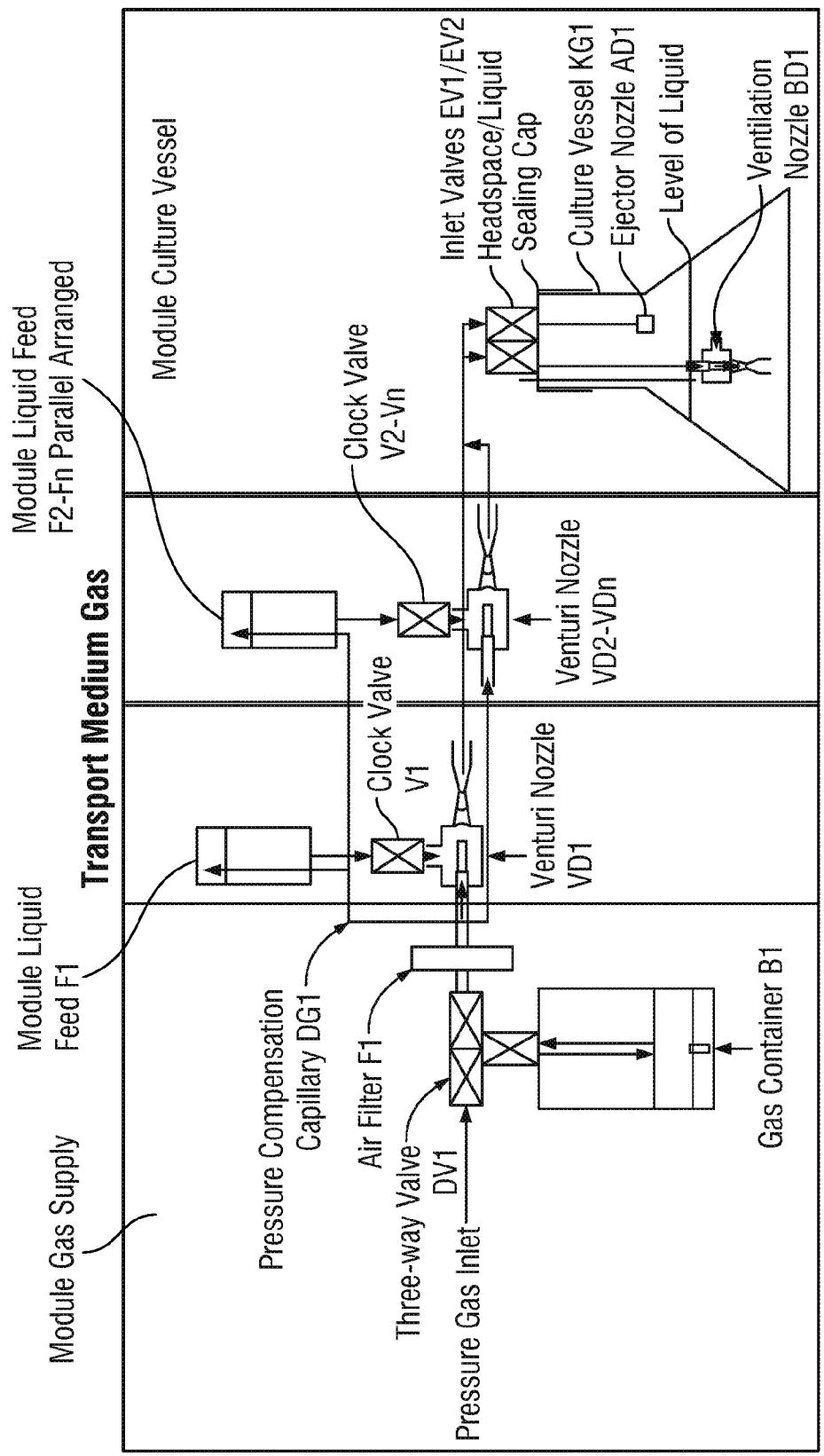
FIG. 5 shows a device comprising at least one module gas supply producing a carrier fluid
Figure 6:
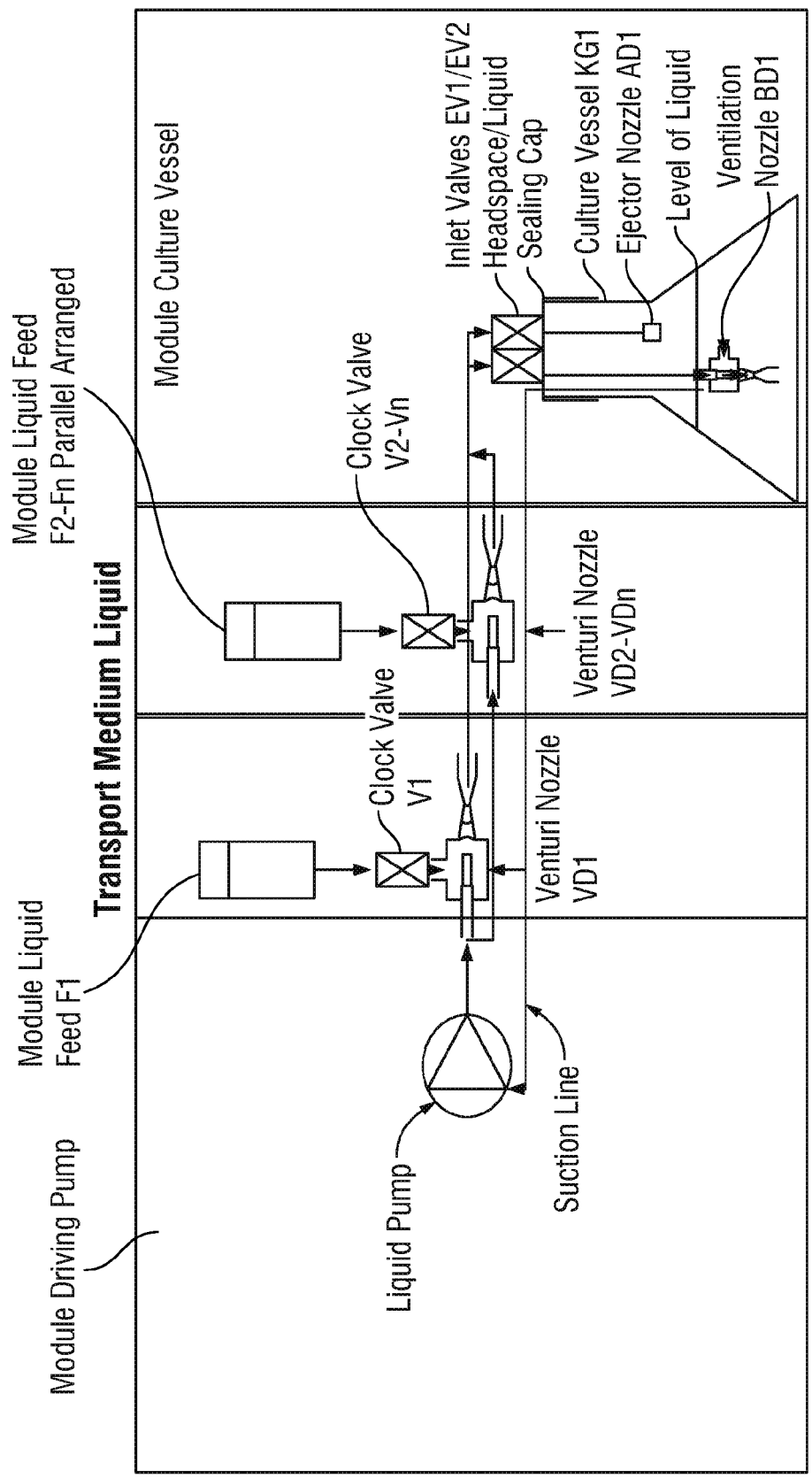
FIG. 6 shows a device comprising at least a module driving pump producing a carrier fluid

Further, there is in so far disclosed a device for dosing gases or liquids or mixtures thereof for use at culture vessels for biological and (bio)chemical reactions, which is characterized by that the device comprises at least one module gas supply according to FIG. 5 or a module driving pump according to FIG. 6 for producing a carrier fluid, a Venturi nozzle which clock valve and liquid feed with a pressure compensation capillary, or a dosage feed for gases, and a supply line, which terminates in the reaction liquid or in the headspace of the culture vessel. The module gas supply or the module driving pump generates a flow of carrier fluid, continuously or discontinuously, through the supply line toward the culture vessel. Further improvements are in any combination characterized by that that the volume of the gas container B1 is between 1 and 40% of the volume of the culture vessel, that the volume of the gas container can be varied by a piston in the range of 0 to 100% of the total volume, that the clock rate of the valve(s) can be adjusted to the "gas hold-up" of the gas bubbles in the culture vessel, preferably is identical thereto, and the amount of the passed-through gas is performed by adjusting the piston, that at least 1 module liquid feed or gas feed according to drawing 1 is installed between the three-way valve and the culture vessel, that the module liquid feed is composed of at least one Venturi nozzle and a liquid container, and the pressure compensation can take place either through the pressure compensation capillary to the gas container or through a connection to the external atmosphere, that the liquid feeds are installed in any position, suspended, standing, lying with regard to the device and always have an air space of at least 2% of the total volume, into which the pressure compensation can take place, that the gas dosage feed is composed of at least one gas inlet, a three-way valve or 2 valves, a gas container with variable internal volume, and a valve opening is connected to a side inlet of a Venturi nozzle, that the dimensions of the components of the device and thus the properties according to the invention can be adjusted to culture vessels from 1 milliliter to 50 liters volume, that by means of the device better mixtures and exchange rates with the reaction liquid are obtained, so that, depending from the kind of cultivation, shaking or stirring of the culture vessel is not necessary, that the tendency to foam formation of the reaction liquid is reduced by the kind of the discontinuous aeration and the gas supply, that by the combination gas/liquid dosage, whether in the reaction liquid or in the headspace of the culture vessel, a shorter mixing time with reaction liquid is achieved, and thus concentration gradients (e.g. substrate) are minimized, that in particular by the dosage into the headspace of the culture vessel, a more effective use of the properties of the dosed liquid takes place, that by the use of the device, the consumption of anti-foam agents can be minimized. For this purpose the gas flow into the reaction liquid is switched off for a short time and changed to the ejector nozzle of the headspace dosage. The flowing-out air "blows" the foam back on the liquid surface. In most cases, this effect is sufficient to reduce the foam generation (in the negative case, a dosage takes place, which in combination with this method can reduce the consumption of anti-foam agents to 10% compared to the prior art), that the thus dosed liquids or a combination of several of them can have an effect on the reaction liquid, e.g. by time-dependent addition of phages to bacteria cultures or growth factors to cell cultures or pH regulation by means of $CO_2$, that the gases dosed in this way are used for generating an artificial atmosphere in the headspace of the culture vessel, e.g. anaerobic atmosphere or enriched with $CO_2$, in a defined composition, that the device is only connected to a power supply and transport medium supply, and all measurement and control parameters are exchanged with the control EDP system via an infrared interface. In all generality, this means a bioreactor for the cultivation of cells, comprising a culture vessel, one or several gas supplies and/or one or several liquid supplies as well as supply devices for gases and/or liquids, by means of which gases and/or liquids can be added to the culture vessel, wherein between the supply device and the gas supply or liquid supply, a mixing device, in particular a Venturi nozzle, for mixing gas and/or liquid from the gas supply or the liquid feed is installed. Gas and liquid can be mixed to an aerosol. Between the mixing device and the gas supply or liquid feed, controllable valves, in particular clock valves, can be installed. Further, this means a method for operating an above bioreactor, wherein a gas or a liquid is used as a carrier fluid, wherein a gas or a liquid is admixed to the carrier fluid in the mixing device, and wherein the proportions of the mixed fluids are defined and are controlled or regulated. The mixed fluids can be added in a defined mass flow to the culture vessel.

The invention claimed is:

1. A bioreactor, comprising a reactor chamber with a closed bottom, a top and a reactor side wall enclosure extending from the bottom to the top, a reactor opening formed at the top of the reactor chamber, and at least one inflatable eddy current breaker installed in the reactor chamber, the inflatable eddy current breaker having two chicanes projecting in from substantially opposed positions on the side wall enclosure and extending from the top toward the bottom of the reactor chamber, the inflatable eddy current breaker further having at least one transverse connecting positions on the chicanes spaced below the top of the reactor chamber and maintaining lower parts of the chicanes in spaced relationship to one another, and wherein the reactor opening may be sealed.

2. A bioreactor according to claim 1, wherein the inflatable eddy current breaker is a constructional unit separate from the reactor walls and in an uninflated collapsed condition is dimensioned to be inserted through the reactor opening and then inflated.

3. A bioreactor according to claim 1, wherein the reactor walls are made of a flexible material, and wherein the reactor walls form a constructional unit with the eddy current breaker.

4. A bioreactor according to claim 3, wherein a multitude of eddy current breakers are provided, which in the inflated condition are stabilized against each other so that the reactor walls form a mechanically stable reaction chamber.

5. A bioreactor according to claim 1, wherein the reactor opening comprises hose lines connected to the eddy current breaker.

6. A bioreactor according to claim 1, wherein the transverse connects lower ends of the chicanes and is inflatable.

7. A bioreactor according to claim 6, wherein the transverse is dimensioned to hold lower parts of the chicanes against the side wall enclosure.

8. A bioreactor according to claim 6, wherein the transverse is substantially annular.

9. A bioreactor according to claim 1, wherein each of the chicanes is cross-sectionally larger at locations closer to the bottom of the reactor chamber.

10. A bioreactor according to claim 1, wherein the reactor opening includes at least one of: means for supplying gases to the reactor chamber, means for supplying liquids to the reactor chamber, means for taking samples from the reactor chamber, means for supplying microorganisms to the reactor chamber, means for supplying cells to the reactor chamber, means for introducing measuring probes to the reactor chamber, means for adding additives to the reactor chamber, means for adding sterilizing agents to the reactor chamber and means for emptying the bioreactor.

11. A bioreactor, comprising a reactor chamber with a closed bottom, a top and a reactor side wall enclosure extending from the bottom to the top, a reactor opening formed at the top of the reactor chamber, and at least two inflatable chicanes adjacent the side wall enclosure at circumferentially spaced-apart positions in the reactor chamber, each of the inflatable chicanes projecting in from the side wall enclosure and extending from the top toward the bottom of the reactor chamber wherein the inflatable chicanes communicate with one another within the reactor chamber via at least one transverse connecting lower parts of the chicanes, the transverse keeping the chicanes against the side wall enclosure.

12. A bioreactor according to claim 11, wherein the side wall enclosure is foldable and the inflatable chicanes define a constructional unit with the side wall enclosure.

* * * * *